United States Patent
Kansagra

(10) Patent No.: US 12,109,364 B2
(45) Date of Patent: *Oct. 8, 2024

(54) DEVICES AND SYSTEMS FOR PROMOTING CONTINUOUS SLEEP OF A SUBJECT AND METHODS OF USING SAME

(71) Applicant: Duke University, Durham, NC (US)

(72) Inventor: Sujay M. Kansagra, Raleigh, NC (US)

(73) Assignee: Duke University, Durham, NC (US)

( * ) Notice: Subject to any disclaimer, the term of this patent is extended or adjusted under 35 U.S.C. 154(b) by 199 days.

This patent is subject to a terminal disclaimer.

(21) Appl. No.: 17/160,821

(22) Filed: Jan. 28, 2021

(65) Prior Publication Data

US 2021/0146091 A1 May 20, 2021

Related U.S. Application Data

(63) Continuation of application No. 16/835,742, filed on Mar. 31, 2020, now Pat. No. 10,940,286.

(Continued)

(51) Int. Cl.
*A61M 21/02* (2006.01)
*A61B 5/00* (2006.01)
*A61M 21/00* (2006.01)

(52) U.S. Cl.
CPC ........... *A61M 21/02* (2013.01); *A61B 5/4809* (2013.01); *A61M 2021/0022* (2013.01);
(Continued)

(58) Field of Classification Search
CPC .......... A61M 21/02; A61M 2021/0022; A61M 2021/0027; A61M 2021/0044;
(Continued)

(56) References Cited

U.S. PATENT DOCUMENTS 6,165,037 A  12/2000  Van
6,175,981 B1  1/2001  Lizama et al.
(Continued)

FOREIGN PATENT DOCUMENTS

EP    3261495 A1    1/2018
WO    2016035073 A1    3/2016
(Continued)

OTHER PUBLICATIONS

Happiest Customer Care Team, "What is the Weaning Feature and when should I use it?", Sep. 6, 2017, happiest baby (Year: 2017).*

(Continued)

*Primary Examiner* — Sunita Reddy
(74) *Attorney, Agent, or Firm* — Myers Bigel, P.A.

(57) ABSTRACT

A method for promoting continuous sleep of a subject by eliminating and/or preventing sleep associations includes: (a) providing an apparatus including at least one sensor and at least one output device; (b) monitoring a state of the subject using the apparatus; (c) determining the subject is in an awake state using the at least one sensor; (d) in response to determining the subject is in the awake state, initiating and maintaining an output using the at least one output device; (e) determining the subject is in a sleep state using the at least one sensor; (f) halting the output in response to determining that the subject is in the sleep state such that the apparatus does not produce any output; (g) repeating at least step (b) during a sleep session. The method further includes modifying an intensity of the output over time until the intensity reaches zero.

18 Claims, 8 Drawing Sheets

Related U.S. Application Data

(60) Provisional application No. 62/827,476, filed on Apr. 1, 2019.

(52) U.S. Cl.
CPC .............. *A61M 2021/0027* (2013.01); *A61M 2021/0044* (2013.01); *A61M 2205/3327* (2013.01); *A61M 2205/3375* (2013.01); *A61M 2205/3584* (2013.01); *A61M 2205/50* (2013.01); *A61M 2205/502* (2013.01)

(58) Field of Classification Search
CPC .. A61M 2205/3327; A61M 2205/3375; A61M 2205/3584; A61M 2205/50; A61M 2205/502; A61M 2209/088; A61M 2240/00; A61B 5/4809; A61B 2503/04
USPC ...................................................... 600/26–28
See application file for complete search history.

(56) References Cited

U.S. PATENT DOCUMENTS

| | | | |
|---|---|---|---|
| 6,280,392 B1 | 8/2001 | Yoshimi et al. | |
| 9,357,855 B2 | 6/2016 | Gersin | |
| 9,629,475 B2 | 4/2017 | Veron | |
| 2006/0102171 A1 | 5/2006 | Gavish | |
| 2007/0279234 A1 | 12/2007 | Walsh | |
| 2008/0191885 A1 | 8/2008 | Loree et al. | |
| 2009/0264715 A1 | 10/2009 | Auphan | |
| 2010/0052918 A1 | 3/2010 | Walker et al. | |
| 2010/0087701 A1* | 4/2010 | Berka ................... | A61M 21/02 600/27 |
| 2010/0094103 A1 | 4/2010 | Kaplan et al. | |
| 2011/0015495 A1 | 1/2011 | Dothie et al. | |
| 2011/0137217 A1* | 6/2011 | Shinnick ............... | A61M 21/00 607/2 |
| 2011/0179546 A1 | 7/2011 | Millette et al. | |
| 2011/0190594 A1 | 8/2011 | Heit et al. | |
| 2011/0295083 A1 | 12/2011 | Doelling et al. | |
| 2012/0092171 A1 | 4/2012 | Hwang et al. | |
| 2014/0163343 A1 | 6/2014 | Heneghan et al. | |
| 2014/0222720 A1 | 8/2014 | Hames et al. | |
| 2014/0250592 A1 | 9/2014 | Karp et al. | |
| 2014/0265480 A1 | 9/2014 | Perrin et al. | |
| 2014/0343354 A1* | 11/2014 | Larson ................. | A61B 5/4812 600/28 |
| 2015/0045608 A1 | 2/2015 | Karp et al. | |
| 2015/0094544 A1 | 4/2015 | Spolin et al. | |
| 2015/0105608 A1 | 4/2015 | Lipoma et al. | |
| 2015/0186609 A1 | 7/2015 | Utter, II | |
| 2015/0258301 A1 | 9/2015 | Trivedi et al. | |
| 2016/0015315 A1 | 1/2016 | Auphan et al. | |
| 2016/0058428 A1* | 3/2016 | Shinar .................. | A61B 5/7267 600/301 |
| 2016/0100696 A1 | 4/2016 | Palashewski et al. | |
| 2016/0151603 A1 | 6/2016 | Shouldice et al. | |
| 2016/0174728 A1 | 6/2016 | Karp et al. | |
| 2016/0183695 A1 | 6/2016 | Maxime | |
| 2016/0217672 A1 | 7/2016 | Yoon et al. | |
| 2016/0270721 A1 | 9/2016 | Raymann et al. | |
| 2016/0292984 A1 | 10/2016 | Pradeep et al. | |
| 2016/0293026 A1 | 10/2016 | Pradeep et al. | |
| 2017/0135632 A1 | 5/2017 | Franceschetti et al. | |
| 2017/0245555 A1 | 8/2017 | Karp | |
| 2017/0251295 A1 | 8/2017 | Pergament et al. | |
| 2017/0258398 A1 | 9/2017 | Jackson | |
| 2017/0347906 A1 | 12/2017 | Intrator | |
| 2017/0347946 A1 | 12/2017 | Arnold et al. | |
| 2018/0078733 A1 | 3/2018 | Freed et al. | |
| 2018/0078735 A1 | 3/2018 | Dalgleish et al. | |
| 2018/0169374 A1 | 6/2018 | Hanson | |
| 2018/0207393 A1* | 7/2018 | Baek ..................... | A61M 21/02 |
| 2018/0303412 A1 | 10/2018 | Moore et al. | |
| 2019/0030278 A1 | 1/2019 | Kremer et al. | |
| 2019/0231256 A1 | 8/2019 | Jantunen | |
| 2019/0247611 A1 | 8/2019 | Karp et al. | |
| 2019/0340515 A1 | 11/2019 | Pathak et al. | |
| 2020/0038623 A1* | 2/2020 | Dalgleish ............. | A61B 5/4812 |
| 2020/0111383 A1 | 4/2020 | Anderson | |
| 2020/0121492 A1 | 4/2020 | Mccreery | |
| 2020/0125036 A1 | 4/2020 | Weiss et al. | |
| 2020/0179206 A1* | 6/2020 | Gadgil ................. | A61F 7/0053 |

FOREIGN PATENT DOCUMENTS

| | | |
|---|---|---|
| WO | 2016110804 A1 | 7/2016 |
| WO | 2016138441 A1 | 9/2016 |
| WO | 2018075566 A1 | 4/2018 |

OTHER PUBLICATIONS

"International Search Report and the Written Opinion of the International Searching Authority corresponding to International Patent Application No. PCT/US20/25939 (14 pages) (mailed Jun. 30, 2020)".

Extended European Search Report for EP application No. 20784149.5 mailed Oct. 26, 2022, 9 pages.

* cited by examiner

DEVICES AND SYSTEMS FOR PROMOTING CONTINUOUS SLEEP OF A SUBJECT AND METHODS OF USING SAME

RELATED APPLICATIONS

This application is a continuation of U.S. patent application Ser. No. 16/835,742, filed Mar. 31, 2020, which claims priority from U.S. Provisional Application No. 62/827,476, filed Apr. 1, 2019, the disclosure of which is incorporated by reference herein in its entirety.

BACKGROUND

It is estimated that 20-30% of young children in the United States have difficulty falling or staying asleep. To understand why this problem may develop, the science behind sleep is important to review. Nighttime sleep occurs in cycles in which we dip into deeper stages of sleep, then emerge into lighter stages at the end of the cycle. There is often an awakening at the end of a sleep cycle during light sleep. A person that "sleeps through the night" is able to simply go back to sleep during the normal nighttime awakenings. This person has the ability to self-soothe, or independently calm his/her awake brain back into the sleep state when more sleep is needed. Some infants, children, and adults cannot self-soothe. They have learned to rely on an external aid to help them fall asleep, known as a sleep association. A sleep association is typically an environmental factor that is associated with the process of falling asleep. The infant, child, or adult learns to go from wake to sleep only when this association is present.

People must learn to fall asleep independently at the beginning of the night so that when they awaken in the middle of the night, they have the ability to self-soothe back to sleep. "Sleep training" is the common name given to the process of teaching an infant that is reliant on a sleep association to fall asleep independently. There are scientifically proven methods for sleep training, with ample studies in the literature that support efficacy and safety. The key to success with sleep training is implementing a persistent, consistent approach over the course of days to weeks. This is challenging for any caregiver.

The need exists for a device that promotes sleep continuity by extinguishing or preventing sleep associations. There is a need for a safe and reliable way to slowly wean associations over the course of days to weeks, thereby training the subject to self-soothe and "sleep through the night."

SUMMARY

The Summary is provided to introduce a selection of concepts that are further described below in the Detailed Description. This Summary is not intended to identify key or essential features of the claimed subject matter, nor is it intended to be used as an aid in limiting the scope of the claimed subject matter.

The present disclosure provides, in part, an apparatus for and a method and system of sleep training a subject.

Accordingly, one aspect of the present disclosure provides an apparatus for sleep training a subject comprising, consisting of, or consisting essentially of means for detecting the state of the subject, means for producing output to sleep train the subject, and a processor in communication with both the means for detection and the means for producing output.

In some embodiments, these components may be incorporated into a mattress, mattress pad, wearable device, bed attachment, bed riser, freestanding module, embedded into a crib/bed, or some combination thereof. The means for detecting the state of the subject include at least one sensor, which in particular embodiments may be physically integrated into and removable from the apparatus. The means for producing output include at least one output device, which in particular embodiments may be physically integrated into and removable from the apparatus. In particular embodiments, the processor is physically integrated into and removable from the apparatus. Various embodiments include a communication device which is electronically connected to the processor and may be physically integrated into and removable from the apparatus. In particular embodiments, the communication device may transmit information to a location external to the apparatus.

Another aspect of the present disclosure provides a method for sleep training a subject by providing an apparatus to the subject comprising, consisting of, or consisting essentially of: (a) capturing data associated with the activity of the subject via an apparatus; (b) determining the state of the subject based on the data; (c) generating and transmitting a notice when the subject is awake or asleep; (c) receiving an instruction indicating an action to be taken by the apparatus; and (d) generating a response emitted by the apparatus.

In particular embodiments, a connected device is configured to receive the notice, determine the response, and transmit the instruction. In some embodiments, these steps are repeated throughout a desired period of time.

In particular embodiments, the duration and type of the response is determined by an algorithm. In particular embodiments, the connected device uses the algorithm to determine the response. In particular embodiments, the algorithm is configured to modify the duration and/or intensity of the response over time and eventually eliminate the output completely.

Various embodiments also allow a caretaker to provide input to the algorithm, causing the algorithm to recalculate the response. Some embodiments allow a caretaker to provide input prior to the first use to configure the algorithm. In particular embodiments, the connected device contains a mobile application, including but not limited to a configuration allowing a caretaker to view data and provide input to the algorithm. Some embodiments include the ability to share data with a remote location, including but not limited to a cloud-based database secured and accessible by authorized users.

Another aspect of the present disclosure provides a system for sleep training a subject by providing an apparatus to the subject comprising, consisting of, or consisting essentially of: (a) at least one sensor to receive input from the subject; (b) at least one output device to produce output to the subject; (c) a connected device configured to receive a notice, determine a response, and transmit an instruction; and (d) a processor configured to receive the input, determine the state of the subject, transmit the notice when the subject is awake, receive the instruction, and generate a response through the at least one output device.

Various embodiments include a communication device configured to transmit the notice and instruction.

In some embodiments, the connected device comprises an algorithm used to generate the instruction.

In particular embodiments, the connected device contains a mobile application configured to allow a caretaker to view data and provide input to customize the response. In some embodiments, the connected device is configured to share data with a remote location, including but not limited to a cloud-based database secured and accessible by authorized users.

Included in this disclosure is the ability to update the algorithm and other software. In some embodiments, this update is facilitated by the communication device. In some embodiments, this update comes from a location external to the apparatus. In particular embodiments, the data from various subjects is used to produce the algorithm and software updates. In some embodiments, this is accomplished by AI or machine learning.

Another aspect of the present disclosure provides all that is described and illustrated herein.

Another aspect of the present disclosure provides a method for promoting continuous sleep of a subject by eliminating and/or preventing sleep associations. The method includes: (a) providing an apparatus comprising at least one sensor and at least one output device; (b) monitoring a state of the subject using the apparatus; (c) determining the subject is in an awake state using the at least one sensor; (d) in response to determining the subject is in the awake state, initiating and maintaining an output that can be detected by the subject using the at least one output device; (e) determining the subject is in a sleep state using the at least one sensor; (f) halting the output in response to determining that the subject is in the sleep state such that the apparatus does not produce any output; (g) repeating at least step (b) during a sleep session. The method further includes modifying an intensity of the output over time until the intensity reaches zero.

In some embodiments, the method is carried out over an entrainment phase and a subsequent sleep training phase, and modifying the intensity of the output over time is carried out during the sleep training phase.

In some embodiments, the method includes: a total amount of time the subject is in the awake state per night; and switching from the entrainment phase to the sleep training phase when the total amount of time the subject is in the awake state is less than a predetermined amount of time on a particular night or on each night of a series of consecutive nights.

In some embodiments, the method includes, when in the sleep training phase: determining a total amount of time the subject is in the awake state per night; decreasing the intensity of the output when the total amount of time the subject is in the awake state is less than a predetermined amount of time on a particular night or on each night of a series of consecutive nights; and repeating the determining and decreasing steps until the intensity of the output is zero. The method may include, when in the sleep training phase: increasing the intensity of the output when the total amount of time the subject is in the awake state is greater than the predetermined amount of time on a particular night or on each night of a series of consecutive nights; and repeating the determining, decreasing, and increasing steps until the intensity of the output is zero.

In some embodiments, the method includes increasing the intensity of the output in response to determining that the subject is in the awake state for longer than a predetermined amount of time.

In some embodiments, the apparatus includes a mattress, a mattress pad configured to be received under a mattress, a mattress pad configured to be received over a mattress, a crib, a device configured to attach to a crib, or a wearable device.

In some embodiments, the at least one sensor includes a microphone and/or an accelerometer.

In some embodiments, the at least one output device comprises an actuator and/or a speaker.

In some embodiments, initiating and maintaining the output is carried out after a predetermined amount of time after continuously determining the subject is in the awake state.

In some embodiments, halting the output is carried out after a predetermined amount of time after continuously determining the subject is in the sleep state.

In some embodiments: the at least one sensor and the at least one output device are each in communication with a processor, determining the subject is in the awake state and determining the subject is in the sleep state are carried out using the processor based on data captured by the at least one sensor, and initiating and maintaining the output and halting the output are carried out in response to instructions generated by the processor. The apparatus may include the processor. The apparatus may include a communication device, and a connected device in communication with the apparatus may include the processor. In some embodiments, the method includes modifying the operation of the apparatus in response to user input on the connected device.

In some embodiments, the method includes: cycling through a plurality of different outputs; determining which particular output or combination of outputs that are most effective for the subject; and using the particular output or combination of outputs that are most effective for the subject as the output.

Another aspect of the present disclosure provides a system for promoting continuous sleep of a subject by eliminating and/or preventing sleep associations. The system includes an apparatus including at least one sensor and at least one output device, and a processor in communication with the at least one sensor and the at least one output device. During an entrainment phase, the processor is configured to: (a) monitor a state of the subject; (b) determine the subject is in an awake state in response to data received from the at least one sensor; (c) in response to determining the subject is in the awake state, direct the at least one output device to initiate and maintain an output that can be detected by the subject; (d) determine the subject is in a sleep state in response to data received from the at least one sensor; (e) direct the at least one output device to halt the output in response to determining that the subject is in the sleep state such that the apparatus does not produce any output; and (f) repeat at least operation (a) during a sleep session. During a sleep training phase that is directly subsequent to the entrainment phase, the processor is configured to modify an intensity of the output over time until the intensity reaches zero.

In some embodiments, the processor is configured to: determine a total amount of time the subject is in the awake state per night; and switch the apparatus from the entrainment phase to the sleep training phase when the total amount of time the subject is in the awake state is less than a predetermined amount of time on a particular night or on each night of a series of consecutive nights.

In some embodiments, the processor is, during the sleep training phase, configured to repeatedly: determine a total amount of time the subject is in the awake state per night; direct the at least one output device to decrease the intensity of the output when the total amount of time the subject is in the awake state is less than a predetermined amount of time on a particular night or on each night of a series of consecutive nights; and optionally direct the at least one output device to increase the intensity of the output when the total amount of time the subject is in the awake state is greater than the predetermined amount of time on a particular night or on each night of a series of consecutive nights.

In some embodiments, the processor is configured to direct the at least one output device to increase the intensity of the output in response to determining that the subject is in the awake state for longer than a predetermined amount of time.

In some embodiments, the apparatus includes a mattress, a mattress pad configured to be received under a mattress, a mattress pad configured to be received over a mattress, a crib, a device configured to attach to a crib, or a wearable device.

In some embodiments, the at least one sensor includes at least one microphone optionally in or connected to a mattress or mattress pad.

In some embodiments, the at least one output device includes an actuator configured to oscillate or vibrate a mattress or mattress pad.

In some embodiments, the at least one output device includes at least one speaker optionally in or connected to a mattress or mattress pad.

In some embodiments, the processor is configured to direct the at least one output device to initiate and maintain the output after a predetermined amount of time after continuously determining the subject is in the awake state.

In some embodiments, the processor is configured to direct the at least one output device to halt the output after a predetermined amount of time after continuously determining the subject is in the sleep state.

The apparatus may include the processor. The apparatus may include a communication device, and the system may include a connected device in communication with the apparatus with the connected device including the processor.

In some embodiments, the system is configured to receive user input to: establish initial settings, select preferred sounds and motions for the output, adjust the predetermined amount of time of continuously determining the subject is in the awake state before the processor directs the at least one output device to initiate and maintain the output, adjust the intensity of the output in real time, select types of sounds of the output, adjust or select a nature of motion of the output, adjust or select a length of time for the entrainment phase, adjust or select a length of time for the sleep training phase, and/or adjust or select the rate of decreasing the intensity of the output during the sleep training phase.

Another aspect of the present disclosure provides an apparatus for promoting continuous sleep of a subject by eliminating and/or preventing sleep associations. The apparatus includes at least one sensor, at least one output device, and a processor in communication with the at least one sensor and the at least one output device. During an entrainment phase, the processor is configured to repeatedly: determine the subject is in an awake state in response to data received from the at least one sensor; in response to determining the subject is in the awake state, direct the at least one output device to initiate and maintain an output that can be detected by the subject; determine the subject is in a sleep state in response to data received from the at least one sensor; and direct the at least one output device to halt the output in response to determining that the subject is in the sleep state such that the apparatus does not produce any output. During a sleep training phase that is directly subsequent to the entrainment phase, the processor is configured to modify an intensity of the output over time until the intensity reaches zero.

BRIEF DESCRIPTION OF THE DRAWINGS

The foregoing aspects and other features of the disclosure are explained in the following description, taken in connection with the accompanying drawings, herein.

DETAILED DESCRIPTION

Figure 1:
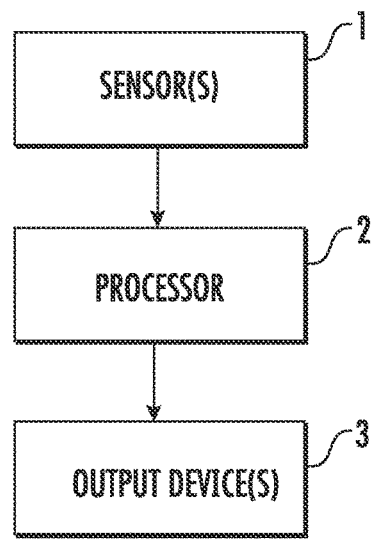
FIG. 1 illustrates the basic components of the device according to various embodiments of the disclosure.

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e. at least one) of the grammatical object of the article. By way of example, "an element" means at least one element and can include more than one element.

"About" is used to provide flexibility to a numerical range endpoint by providing that a given value may be "slightly above" or "slightly below" the endpoint without affecting the desired result.

The use herein of the terms "including," "comprising," or "having," and variations thereof, is meant to encompass the elements listed thereafter and equivalents thereof as well as additional elements. Embodiments recited as "including," "comprising," or "having" certain elements are also contemplated as "consisting essentially of" and "consisting of" those certain elements. As used herein, "and/or" refers to and encompasses any and all possible combinations of one or more of the associated listed items, as well as the lack of combinations where interpreted in the alternative ("or").

As used herein, the transitional phrase "consisting essentially of" (and grammatical variants) is to be interpreted as encompassing the recited materials or steps "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising."

Moreover, the present disclosure also contemplates that in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

It is noted that any one or more aspects or features described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

As used herein, "treatment," "therapy" and/or "therapy regimen" refer to the clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder or condition. As used herein, the term "sleep training," "sleep train," "promoting continuous sleep," and any variations thereof refer to the practice of training a subject to fall asleep on their own and sleep throughout a period of time without requiring caregiver intervention.

As used herein, the term "sleep association" (also referred to as "sleep-onset association") refers to a specific stimulation, object, or setting that is associated with the process of falling asleep. There can be both positive sleep associations and negative sleep associations. Positive sleep associations are typically present the entire night and don't cause sleep interruption. For example, a positive sleep association may be a white noise machine that stays on all night, a specific pillow/blanket, a bed partner, etc. Negative sleep associations are only present at the beginning of the night, and have to be put back in place during normal nighttime awakenings. This includes caregiver intervention for sleep (such as rocking, holding, feeding), a TV that is set to turn off with a timer, a specific song, etc.

As used herein, the term "subject" and "patient" are used interchangeably herein and refer to both human and nonhuman animals. A subject is preferably a human, and in some embodiments may be an infant. In some embodiments the subject may be a human suffering from a sleep disorder. The term "nonhuman animals" of the disclosure includes all vertebrates, e.g., mammals and non-mammals, such as nonhuman primates, sheep, dog, cat, horse, cow, chickens, amphibians, reptiles, and the like. A sleep disorder refers to any disorder that affects, disrupts, or involves sleep.

As used herein, the term "caretaker" and "authorized user" and any variations thereof are used interchangeably herein and refer to humans with caretaking responsibilities over the subject, both medical and non-medical. An authorized user may include, for example, a medical professional, healthcare worker and the like who are treating or otherwise providing care to the subject.

As used herein, the term "state" and any variations thereof refer to the particular condition of a subject at a specific time, for example, awake or asleep.

As used herein, the term "electronic communication" and any variations thereof mean any connection, both physical and otherwise, that allow transmission of information in any form between the two objects which are electronically connected. This includes but is not limited to a wired connection, a network connection, or any other type of wireless connection.

As used herein, the term "connected device" and any variations thereof refer to a device external to the apparatus which can communicate with the apparatus, for example, through an electronic or network connection.

As used herein, the term "cloud-based database" and any variations thereof refer to a structured set of data held on an external server and accessible from any remote location using a network connection.

Unless otherwise defined, all technical terms used herein have the same meaning as commonly understood by one of ordinary skill in the art to which this disclosure belongs.

The present disclosure provides, in part, an apparatus for and a method and system of sleep training a subject.

Apparatus

One aspect of the present disclosure provides an apparatus comprising, consisting of, or consisting essentially of at least one sensor for detecting the state of the subject, at least one device for producing output to the subject, and a processor in communication with both the one or more sensor and one or more output device, as shown in FIG. 1.

In some embodiments of the present disclosure, each of the one or more sensors [1] may be selected from the group comprising a microphone, an accelerometer, a temperature sensor, a light sensor, a pressure sensor, and any combinations thereof. This allows for detection of the state of the subject based on various metrics, such as movement, sound, and location, indicating if the subject is moving, crying, if there is a light present, or if the subject is on or near the device.

In some embodiments of the present disclosure, the processor [2] is connected to and in communication with the one or more sensors [1] and receives data from any sensors, such as movement, pressure, sound, or light. This data is used to determine the state of the subject. For example, if the processor receives data from the sensors indicating a specific pattern of sound, the subject may be crying. From this type of data, the processor [2] may determine that the subject is awake. In contrast, a lack of sound, movement, or other data may indicate that the subject is asleep. If the sensor data indicates that the subject is awake, the processor [2] then generates an instruction which is sent to the one or more output devices [3] and produces an output to the subject. The processor [2] may be selected from the group comprising a microcontroller, a microprocessor, a system-on-chip, and any combinations thereof.

In some embodiments of the present disclosure, each of the one or more output devices [3] is connected to and in communication with the processor [2] and receives instructions from the processor, triggering a specified output. Each of the one or more output devices [3] may be selected from the group comprising a mechanical actuator such as a vibrator or shaker that vibrates or shakes the sleeping surface or a device that rocks or oscillates the sleeping surface, a speaker, a light-emitting device, a smell-emitting device, and any combinations thereof. This allows for the subject to be exposed to a variety of outputs, such as sound, light, vibration, and motion. The output produced by the one or more output devices [3] then soothes the subject from a waking state to a sleeping state.

Additionally, in some embodiments of the present disclosure, the processor [2] may contain an algorithm which is configured to dictate the duration and type of output produced by the one or more output devices [3].

One advantage is the automatic nature of the apparatus. According to one embodiment, the algorithm is configured to automatically modify the duration and/or intensity of the output with each use, over time, in order to eventually stop the output completely. This is accomplished with minimal caretaker action; for example, in some embodiments, the caretaker provides input to initialize the algorithm prior to the first use of the apparatus. In other embodiments, the caretaker has the option to provide ongoing input, causing the algorithm to recalculate the output in order to conform to caretaker preferences.

Figure 2:
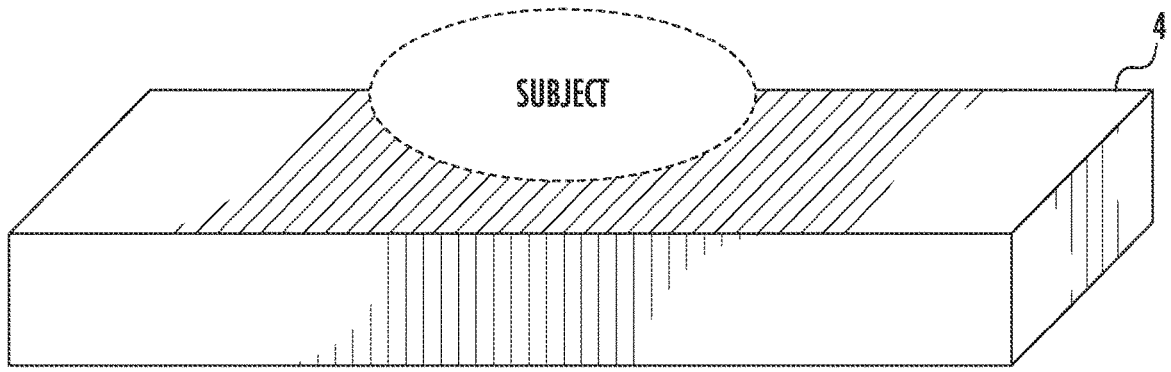
FIG. 2 illustrates a mattress according to various embodiments of the disclosure.
Figure 3:
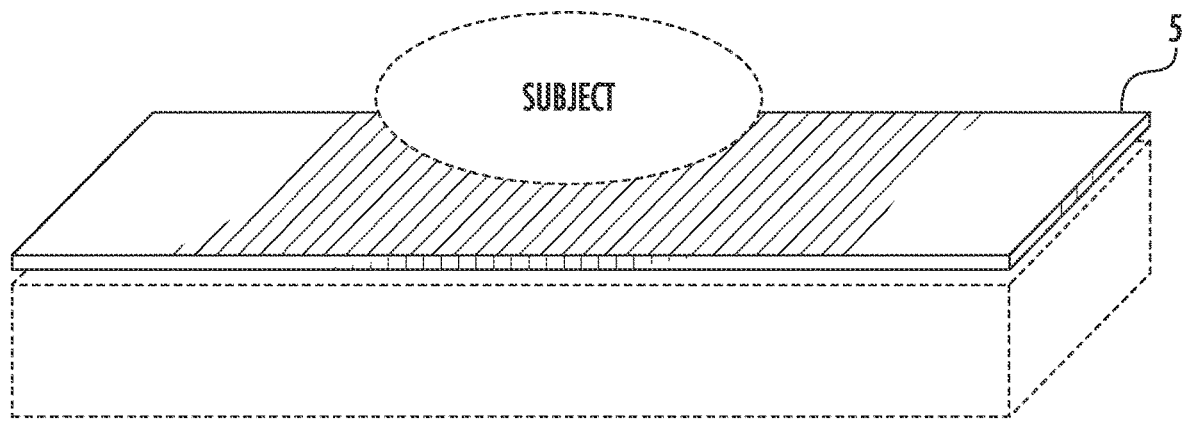
FIG. 3 illustrates a mattress pad according to various embodiments of the disclosure.
Figure 4:
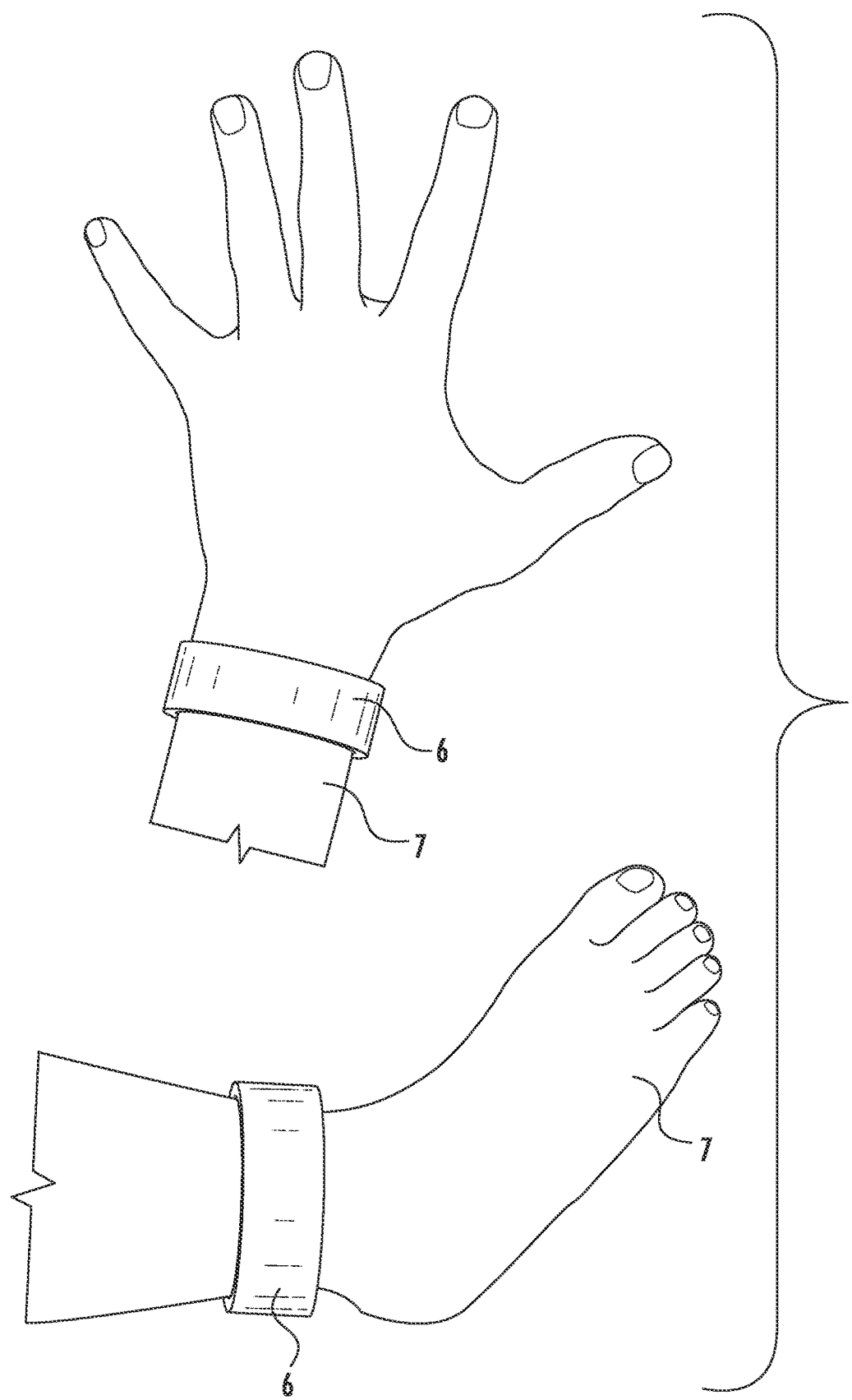
FIG. 4 illustrates wearable devices according to various embodiments of the disclosure.

As shown in FIGS. 2-4, in some embodiments of the present disclosure, any or all of the components (including the one or more sensors [1], processor [2], and one or more output devices [3]) may be incorporated into a housing which embodies the apparatus. In some embodiments, one or more components may be physically integrated into and optionally removable from the housing. In some embodiments of the present disclosure, the housing may include a mattress, mattress pad, wearable device, bed attachment, bed riser, freestanding module, or any combinations thereof.

In one embodiment, and as shown in FIG. 2, the housing comprises a mattress [4]. In another embodiment, and as shown in FIG. 3, the housing comprises a mattress pad, mat, cushion, or similar configuration on which a subject sleeps [5] that includes a pad placed on top of, and removable from, a mattress. As shown in FIG. 4, a wearable device [6] includes a device that is worn on the body of the subject [7], including but not limited to on the wrist, hand, arm, ankle, leg, or foot. In another embodiment, the apparatus comprises a bed attachment. As used herein, the term "bed attachment" includes any device that is designed to attach to, or be in communication with, a bed. For example, in one embodiment, the bed attachment attaches to the side of a crib, where it is able to detect input from the subject and produce output to the subject by providing vibrations to the crib. In another embodiment, the bed attachment comprises a bed riser that is positioned between the feet of a bed and the floor. In another embodiment, the device is a freestanding module separate from and external to the subject and any sleep surfaces, where it is able to detect sound input from and produce sound output to the subject. Each embodiment enables the apparatus to effectively detect the state of the subject and provide output to the subject while in use.

Systems

Figure 5:
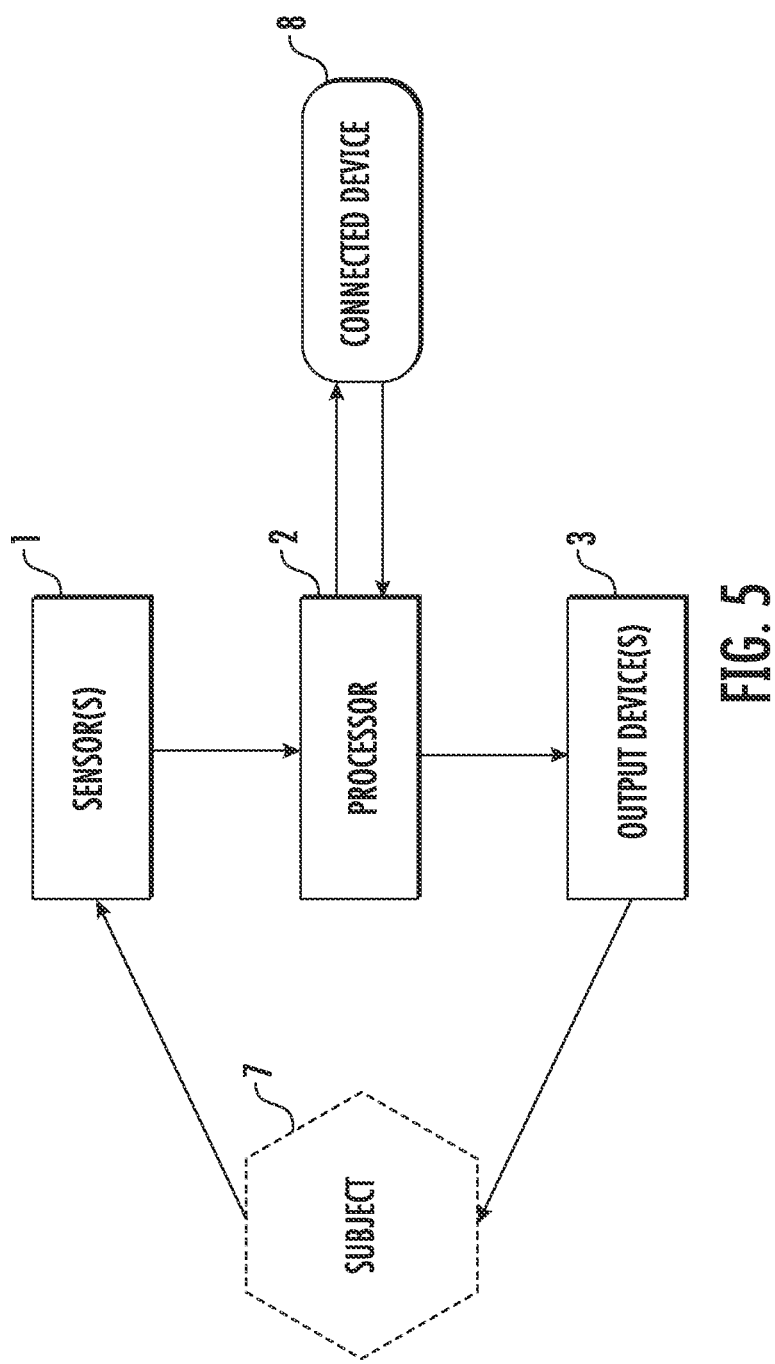
FIG. 5 illustrates a diagram of the system according to various embodiments of the disclosure.

The apparatuses of the present disclosure may be part a larger sleep training system. Accordingly, another aspect of the present disclosure provides a system for sleep training a subject. As shown in FIG. 5, the system comprises, consists of, or consists essentially of at least one sensor [1] configured to detect input from the subject; at least one output device [3] configured to produce output to the subject; and a processor [2] configured to receive the input from the one or more sensors [1], determine the state of the subject based on the input, produce an instruction, and generate a response through the one or more output devices [3]. In some embodiments of the present disclosure, the processor [2] comprises an algorithm used to generate the instruction.

In various embodiments of the present disclosure, the system further comprises a communication device that is in electronic communication with the processor [2] and enables communication of information to a location external to the apparatus. The communication device may be selected from the group comprising a wireless transceiver, a near field communication chipset, a Bluetooth chipset, an Ethernet chipset, a radio, and any combinations thereof. In some embodiments, the communication device enables wireless communication between the apparatus and other devices external to the apparatus.

Figure 8:
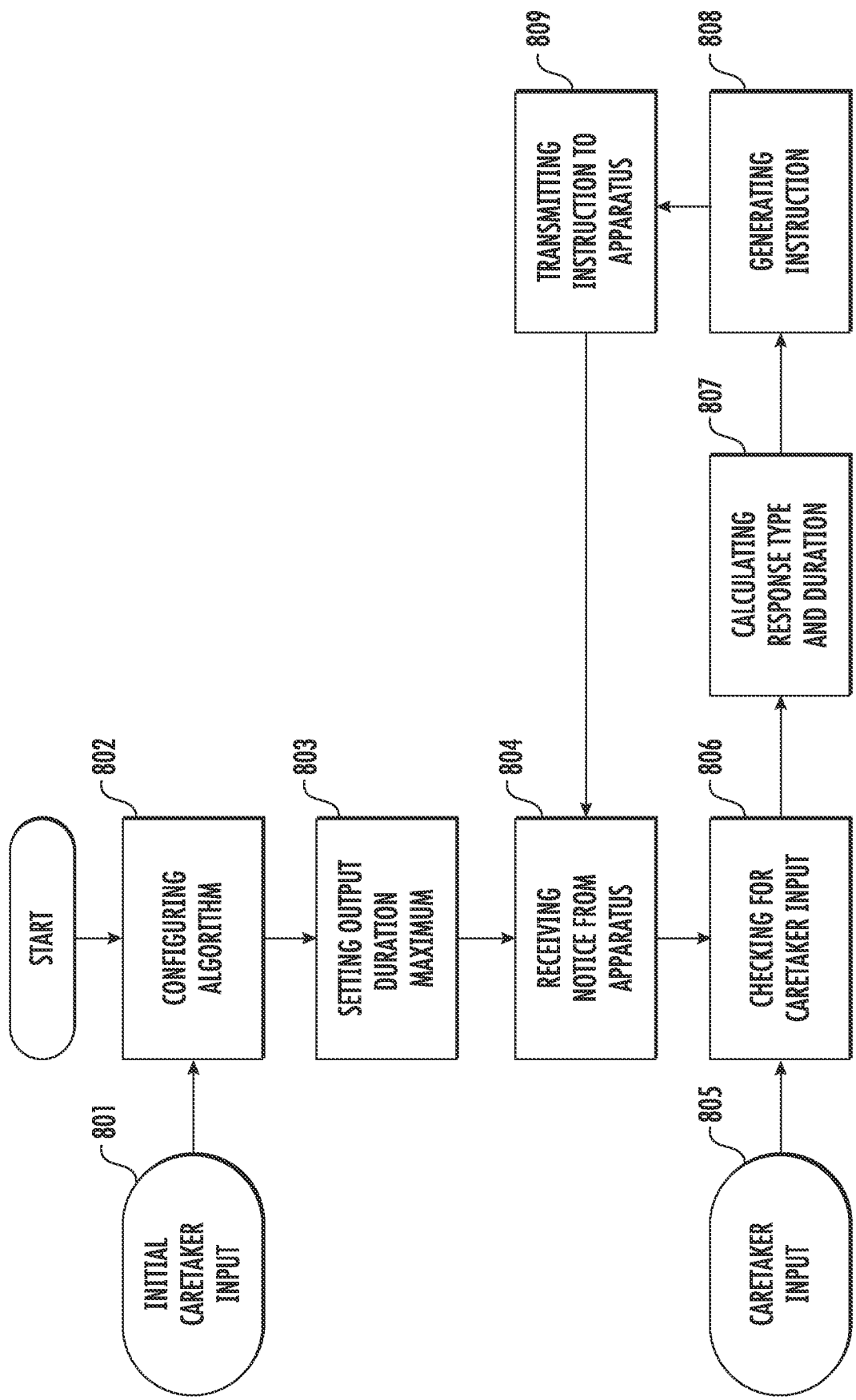
FIG. 8 illustrates a flow diagram of the method according to various embodiments of the disclosure.

In some embodiments of the present disclosure, as shown additionally in FIG. 8, the system additionally includes a connected device [8] comprising the algorithm and configured to receive the notice [804] from the processor, determine the response using the algorithm [807, 808], and transmit the instruction [809] back to the processor. Also in these embodiments, the communication device is configured to transmit the notice and instruction between the processor [2] and connected device [8] or other locations external to the apparatus.

The present disclosure additionally describes an embodiment wherein the connected device [8] comprises a mobile application configured to allow a caretaker to view data associated with the system and apparatus. Additionally, the caretaker may provide input to the algorithm using the mobile application in order to initialize the system prior to the first use of the apparatus or at any point during its use in order to customize the instruction and response. See, e.g., FIG. 8 [801, 805].

One advantage is the automatic nature of the system. According to one embodiment, the algorithm is configured to automatically modify the duration and/or intensity of the output with each use, over time, in order to eventually stop the output completely. This is accomplished with minimal caretaker action; for example, in some embodiments, the caretaker provides input to initialize the algorithm prior to the first use of the apparatus. In other embodiments, the caretaker has the option to provide ongoing input, causing the algorithm to recalculate the output in order to conform to caretaker preferences. See, e.g., FIG. 8 [801, 805].

Figure 6:
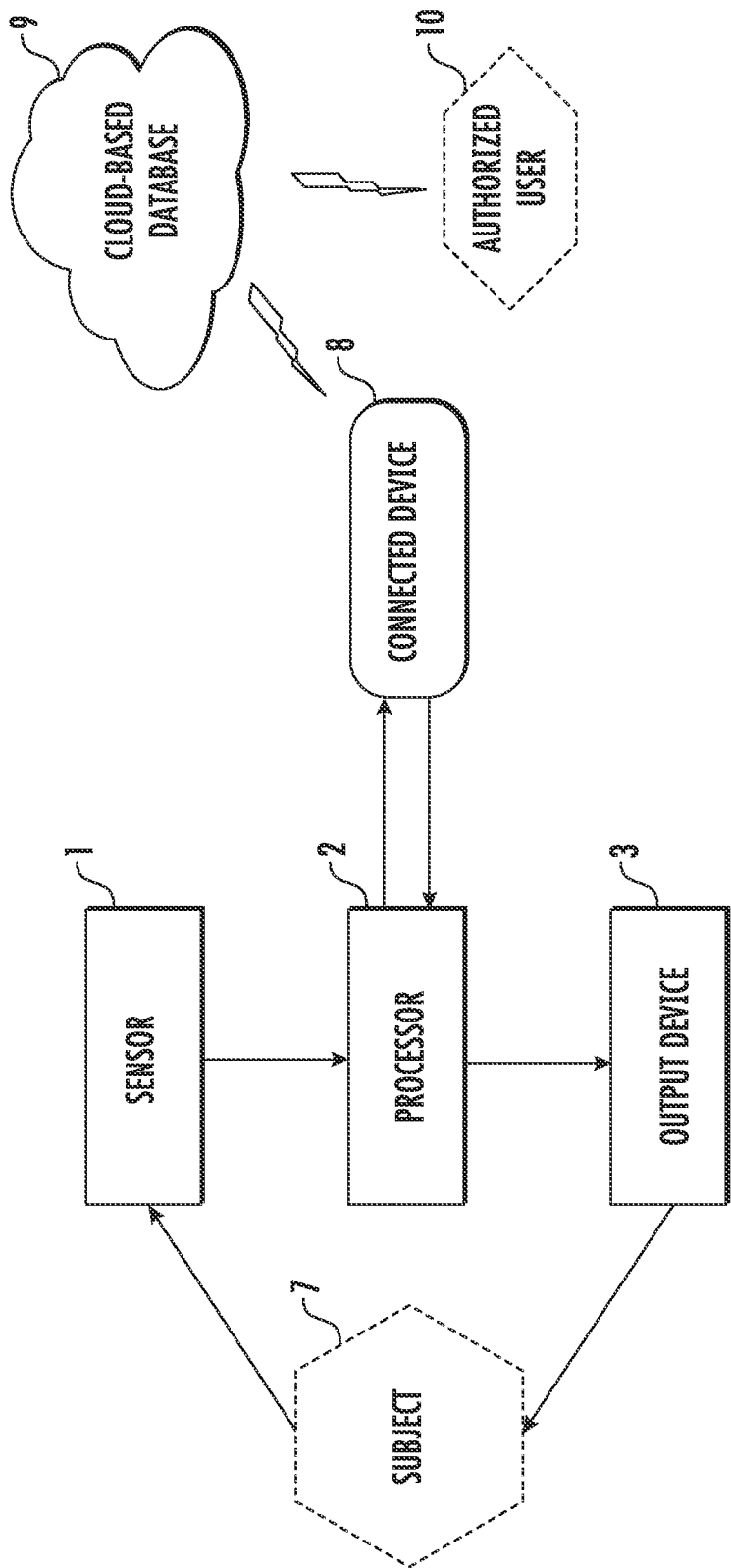
FIG. 6 illustrates a diagram of the system according to various embodiments of the disclosure.

As shown in FIG. 6, in some embodiments of the present disclosure, the connected device [8] or the communication device may be configured to share data with a remote location. In one embodiment, the remote location comprises a cloud-based database [9]. Any such data is secured and may be accessed by authorized users [10].

In some embodiments of the present disclosure, all components of the system may be connected electronically, physically, wirelessly, or by any other method which enables the system described in the present disclosure.

Methods of Use

Figure 7:
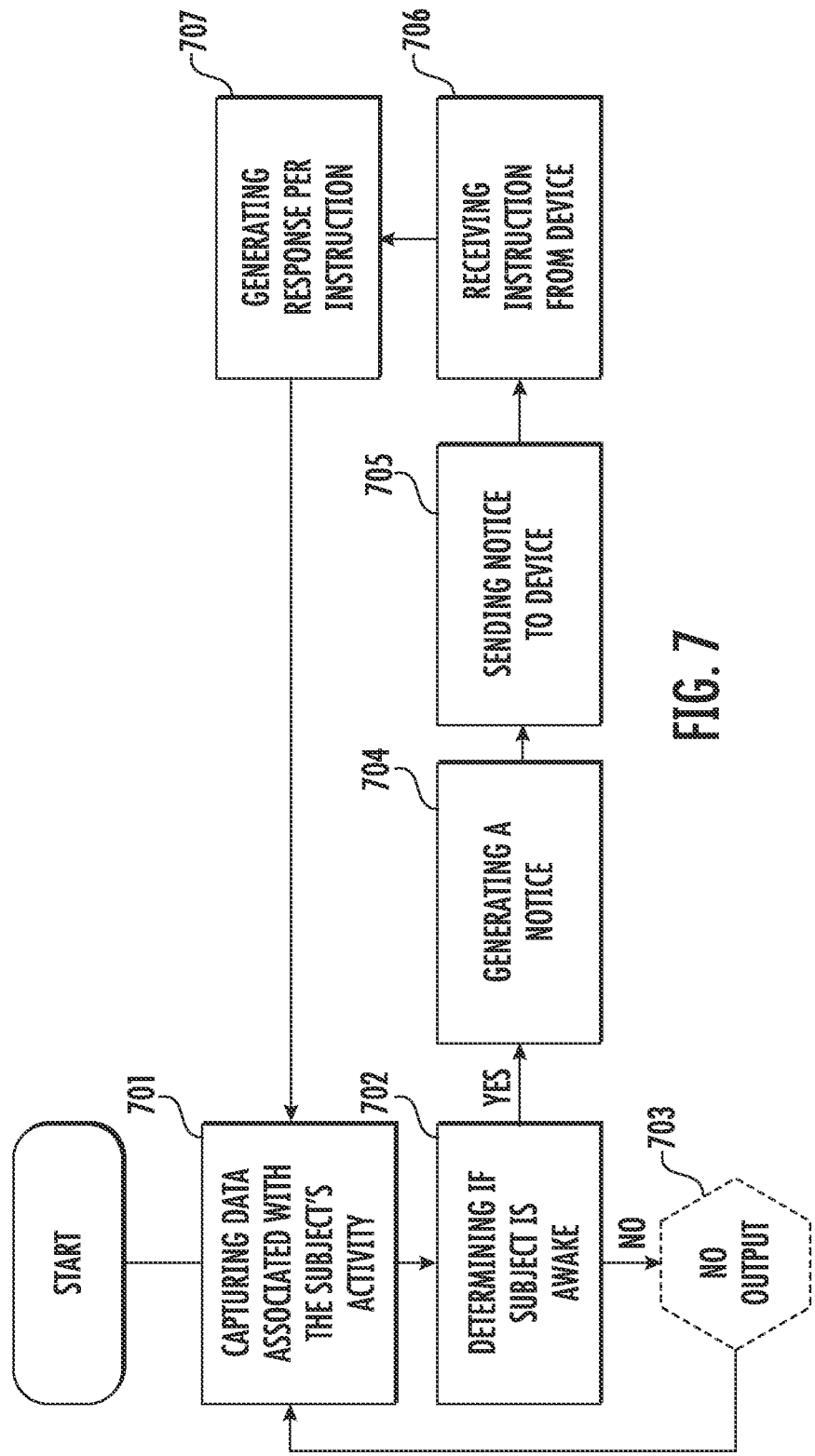
FIG. 7 illustrates a flow diagram of the method according to various embodiments of the disclosure.

Another aspect of the present disclosure, as shown in FIGS. 7 and 8, provides a method for sleep training a subject comprising, consisting of, or consisting essentially of (a) capturing data associated with the activity of the subject from the one or more sensors of the apparatus [701]; (b) determining the state of the subject based on the data [702]; (c) generating a notice when the subject is awake [703, 704]; (d) producing an instruction indicating an action to be taken by the apparatus, including its type and duration [808]; and (e) generating a response emitted through the one or more output devices based on the instruction [707]. In some embodiments of the present disclosure, these steps are repeated throughout a desired period of use.

In particular embodiments of the present disclosure, the instruction is determined by an algorithm. The algorithm may be configured to automatically reduce the duration of the response at the start of each use until the duration reaches zero [803]. This is an embodiment of the "weaning" process used to sleep train the subject automatically. By reducing the duration of the response generated when the subject is awake, the subject is gradually weaned off of the stimuli used to soothe the subject to sleep and is able to self-soothe continuously throughout the night.

In other embodiments of the present disclosure as shown in FIG. 8, a caretaker may provide input to the algorithm. In one embodiment, the input may be provided prior to the first use of the apparatus and used to configure the algorithm based on parameters and preferences of the caretaker [801]. For example, a caretaker may set a preferred output, start the entrainment process as provided herein at a particular output duration/intensity, or increase or decrease the speed of the sleep-training process as provided herein, e.g. how rapidly the output duration and/or intensity is modified by the algorithm. In another embodiment of the present disclosure, the input may be provided at any point throughout the use of the apparatus and used by the algorithm to recalculate the following instructions based on parameters and preferences of the caretaker [805]. For example, a caretaker may wish to change the preferred output based on effectiveness or modify the "aggressiveness" of the sleep-training process based on results or other factors.

In some embodiments of the present disclosure, machine learning or artificial intelligence may be used to update or modify the algorithm. For example, data from previous uses may be used by AI to modify the algorithm and tailor the response to the subject and increase its effectiveness. Additionally, data from other subjects may be incorporated into the AI system in order to improve the general effectiveness.

In another embodiment, the processor is further configured to classify data indicating the state of the subject into at least one of a plurality of categories based on a classification rule, and the output for the subject is determined based on the classification of the data indicating the state of the subject.

In one embodiment, the classification rule is based on one or more machine learning algorithms trained on one or more training examples. In some embodiments, the one or more machine learning algorithms correspond to one or more of the following: gradient tree boosting algorithm, a random forest algorithm, support vector machine algorithm, a penalized logistic regression algorithm, a C5.0 algorithm, and combinations thereof.

Furthermore, in other embodiments of the present disclosure, any software and firmware used in the apparatus, in addition to the algorithm, may be updated as necessary or desired. Such updates may be accomplished wirelessly, remotely, or by any other method.

In some embodiments of the present disclosure, a method or algorithm for promoting continuous sleep of a subject by eliminating and/or preventing sleep associations includes an entrainment phase and a subsequent sleep training phase.

The entrainment phase may have a length of between three (3) and 30 days and, in some embodiments, has a length of about a week or seven days.

During the entrainment phase, when the apparatus detects the child is awake and/or crying for a predetermined or pre-specified period of time, the apparatus may produce a consistent output of sound and/or motion (or both sound and motion) to sooth the child back to sleep. The predetermined period of time may be between five (5) and 20 seconds and, in some embodiments, is about 10 seconds.

As described above, the apparatus may include at least one sensor and at least one output device. The sensor(s) may include at least one accelerometer and/or at least one microphone. In some embodiments, the sensors include a microphone, a first accelerometer in a first location of a mattress or mattress pad (e.g., a first end portion of the mattress or mattress pad), and a second accelerometer in a second location of the mattress or mattress pad (e.g., a second opposite end portion of the mattress or mattress pad). The output device(s) may include an actuator, shaker, or vibrator configured to vibrate the mattress or mattress pad and/or at least one speaker configured to output a soothing sound (e.g., white noise, heartbeat, soft music, etc.).

The apparatus may continue to analyze whether the child is awake and/or crying while the apparatus is outputting sound and/or motion. If the child continues to be awake and/or cry, the intensity of the sound and/or motion may be steadily increased up to a maximum output level. Once the apparatus detects that the child is asleep, the apparatus slowly reduces the output over a period of time (e.g., 30 to 60 seconds) and turns off, so no sound or motion is provided while the child is asleep. This process repeats with each awakening. This is the entrainment phase.

After about one week, the child should be "trained" to go back to sleep with the apparatus instead of needing a caregiver such as a parent to go back to sleep. Once the apparatus detects that the total minutes of awake time and/or crying each night is minimal (e.g., less than five minutes), the apparatus enters the sleep training phase.

During the sleep training phase, when the apparatus detects wakefulness, the intensity of the output may be slightly less than the intensity of the output used the night before. For example, if the child received a "level 10" output for both sound and motion, then the maximum the apparatus may provide is "level 9." As long as the child is not crying excessively at a given level, each night the output will be slightly less than the preceding night, until over period of time (e.g., three to four weeks), the intensity of the output has decreased all the way down to zero (no output). At that point, the child will be relying on internal self-soothing mechanisms to get to sleep, thereby completing the sleep training process. However if crying during sleep training phase exceeds a certain threshold for a night (or over series of multiple nights), then the entrainment phase may restart.

Some known sleep products claim to help "sleep train" infants, but actually promote sleep associations by incorporating outputs such as white noise and motion the entire night. Many previous studies have determined that the key to sleep training is to wean off of such sleep associations over time.

In some embodiments, instead of a steady wean during the sleep training phase, the underlying algorithm can be modified to have cutoffs of crying and/or wakefulness, so that if a child is crying and/or awake for too long on any given night during the sleep training phase, it may temporarily increase the intensity of the sound and/or motion. In this way, the algorithm may be considered as more of a responsive modification rather than simply "weaning" of output.

In some embodiments, any of the measured metrics can be modified to change the overall responsiveness of the apparatus. For example, the length of time crying needed to start the apparatus (e.g., initiate output), the intensity of the output, the type(s) of sounds, the nature of the motion, the length of each phase, and/or the rate of wean/modification can be changed by adjusting the algorithm or software (e.g., by user input on the connected device).

In some embodiments, the apparatus can incorporate user input from a caregiver such as a parent using a mobile application on the connected device. For example, parents could be asked about what sounds and/or motions they prefer to use. Also, parents could be asked about their comfort level with the child crying. This parental input can change which outputs are used and the rate of wean/modification.

In some embodiments, the underlying algorithm can implement machine learning and cycle through various sounds and motions to determine which one or which combination the child responds to best. Once learned, the apparatus may only use those outputs that the child finds the most soothing.

In some embodiments, the apparatus gathers data on a variety of metrics, such as which sounds and/or motions are being used, how long the child cried each night, the length of output each night, etc. This data may be used to modify the algorithm.

Figure 9:
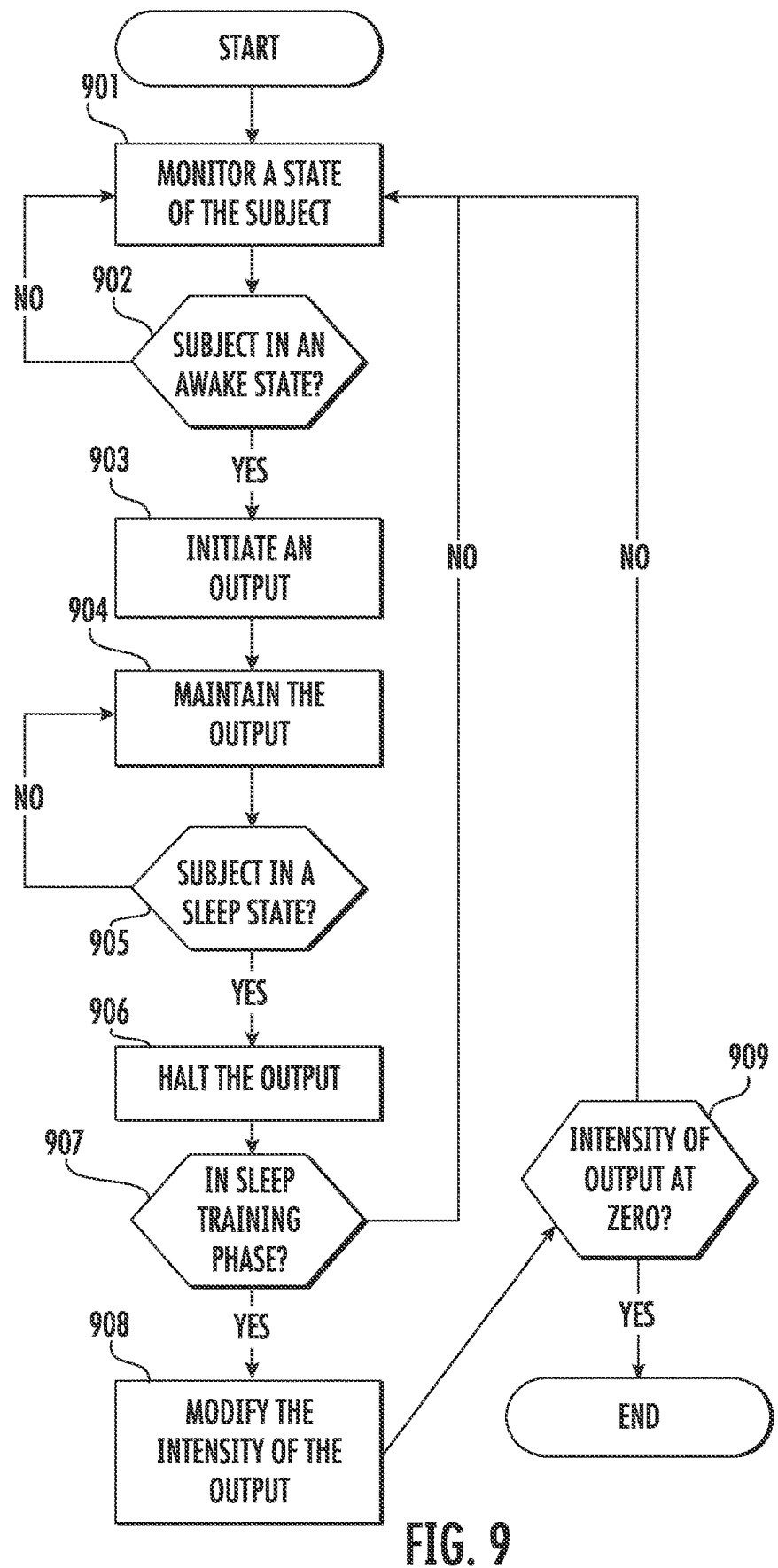
FIG. 9 illustrates a flow diagram of the method according to various embodiments of the disclosure.

Another aspect of the present disclosure, as shown in FIG. 9, provides a method for promoting continuous sleep of a subject by eliminating and/or preventing sleep associations including (a) providing an apparatus comprising at least one sensor and at least one output device (e.g., the apparatus according to embodiments described herein); (b) monitoring a state of the subject using the apparatus [901]; (c) determining the subject is in an awake state using the at least one sensor [902]; (d) in response to determining the subject is in the awake state, initiating and maintaining an output that can be detected by the subject using the at least one output device [903, 904]; (e) determining the subject is in a sleep state using the at least one sensor [905]; (f) halting the output in response to determining that the subject is in the sleep state such that the apparatus does not produce any output [906]; and repeating at least step (b) during a sleep session. In some embodiments, steps (b) through (f) are repeated at least once during a sleep session and, in some embodiments, steps (b) through (f) are repeated a plurality of times during a sleep session (e.g., based on the number of times the subject is determined to be in the awake state during the sleep session).

The method includes modifying an intensity of the output over time until the intensity reaches zero [908, 909]. As described above, the method may be carried out over an entrainment phase and a subsequent sleep training phase, and the step of modifying the intensity of the output over time may be carried out during the sleep training phase [907]. In some embodiments, the entrainment phase has a length of between 3 days and 30 days. In some embodiments, the sleep training phase has a length of between 3 days and 30 days.

In some embodiments, the method includes: determining a total amount of time the subject is in the awake state per night; and switching from the entrainment phase to the sleep training phase when the total amount of time the subject is in the awake state is less than a predetermined amount of time (e.g., 5 minutes) on a particular night or on each night of a series of consecutive night.

As used herein, the term "night" may mean a primary period of sleep or overnight sleep period (e.g., as opposed to naps). The night may span consecutive days. For example and without limitation, a "night" may be from 8:00 pm on a first day to 8:00 am on a second, directly subsequent day.

In some embodiments, the method includes, when in the sleep training phase: determining a total amount of time the subject is in the awake state per night; reducing the intensity of the output when the total amount of time the subject is in the awake state is less than a predetermined amount of time on a particular night or on each night of a series of consecutive nights; and repeating the determining and reducing steps until the intensity of the output is zero. The method may include, when in the sleep training phase: increasing the intensity of the output when the total amount of time the subject is in the awake state is greater than the predetermined amount of time on a particular night or on each night of a series of consecutive nights; and repeating the determining, decreasing, and increasing steps until the intensity of the output is zero. Thus, as described above, the underlying algorithm may provide more of a responsive modification rather than simply "weaning" of output.

In some embodiments, the method includes increasing the intensity of the output in response to determining that the subject is in the awake state for longer than a predetermined amount of time. For example, if the subject is awake and/or crying for more than five minutes, the intensity of the output may be increased. This may occur during the entrainment phase or during the sleep training phase.

In some embodiments, initiating and maintaining the output [903, 904] is carried out after a predetermined amount of time (e.g., 3 to 60 seconds) after continuously determining the subject is in the awake state. In some embodiments, halting the output [906] is carried out after a predetermined amount of time (e.g., 5 to 60 seconds) after continuously determining the subject is in the sleep state.

The at least one sensor and the at least one output device may each be in communication with a processor. The steps of determining the subject is in the awake state [902] and determining the subject is in the sleep state [905] may be carried out using the processor based on data captured by the at least one sensor. The steps of initiating and maintaining the output [903, 904], halting the output [906], and/or modifying the intensity of the output may be carried out in response to instructions generated by the processor. As described herein, the instructions may be generated by an algorithm in the processor.

In some embodiments, the apparatus includes the processor. In some embodiments, the apparatus includes a communication device such as a transceiver, and a connected device in communication with the apparatus includes the processor. As described herein, the operation of the apparatus may be modified in response to user input on the connected device.

Figure 10:
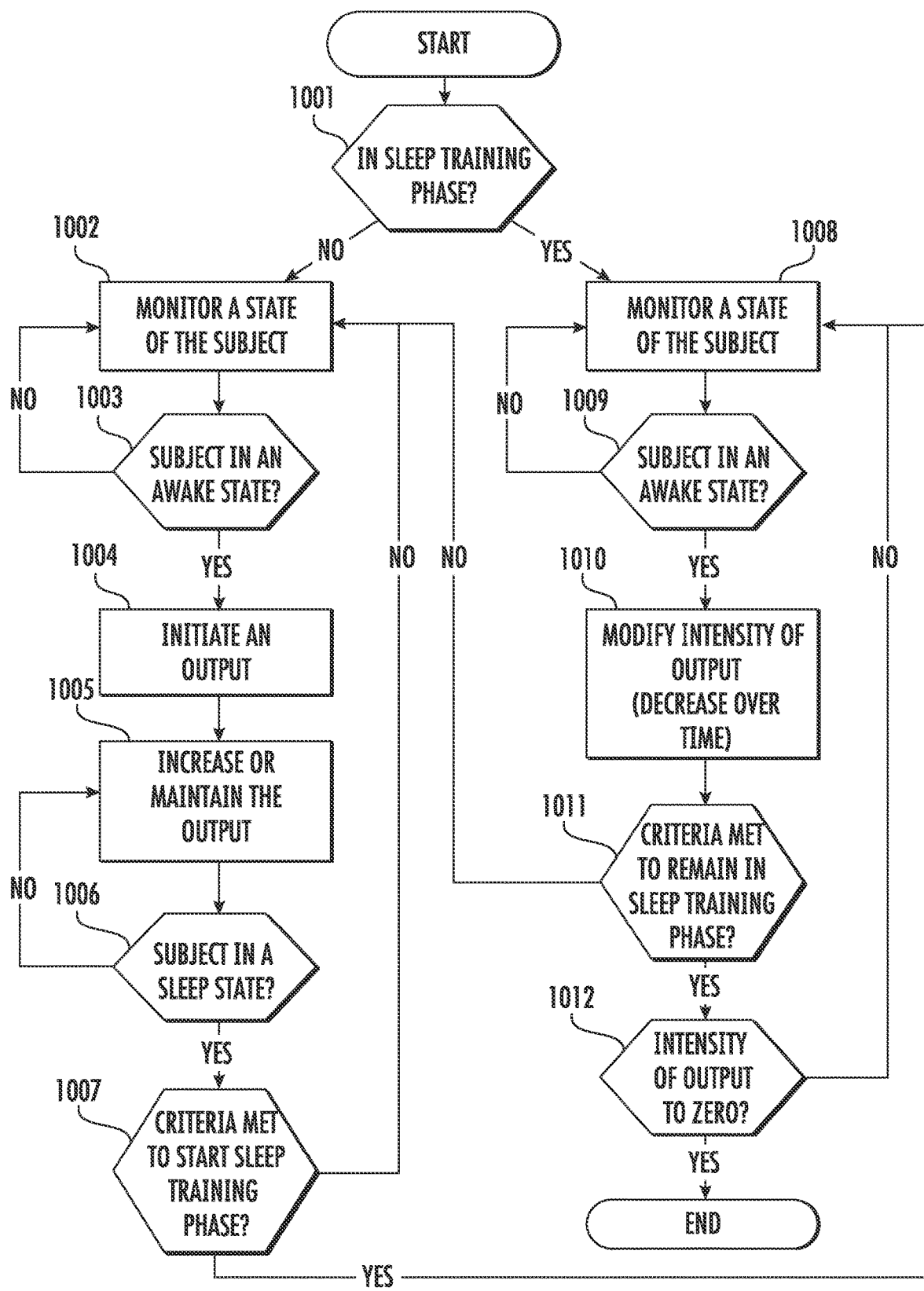
FIG. 10 illustrates a flow diagram of the method according to various embodiments of the disclosure.

Another aspect of the present disclosure, as shown in FIG. 10, provides a method for promoting continuous sleep of a subject by eliminating and/or preventing sleep associations. The method includes determining if the apparatus is in the sleep training phase [1001]. If the apparatus is not in the sleep training phase, i.e., the apparatus is in the entrainment phase, the method includes monitoring a state of the subject [1002]. If it is determined that the subject is in the awake state [1003], the method includes initiating an output [1004] and maintaining the output and/or increasing the intensity of the output [1005]. As described herein, the intensity of the output may be increased if it is determined that the subject is in the awake state for longer than a predetermined amount of time. Also as described herein, the output may be halted in response to determining that the subject has returned to the sleep state.

The method includes determining if the subject has met the criteria to begin the sleep training phase [1006, 1007]. This determination may be made, for example, based on how long the subject was in the awake state on a particular night or on each night of a series of consecutive nights.

If the criteria has been met to start the sleep training phase, the method includes monitoring a state of the subject [1008] and determining if the subject is in the awake state The method includes modifying the intensity of the output [1010] including decreasing the intensity over time.

The method includes determining if the criteria has been met for the subject to remain in the sleep training phase [1011]. If not, the apparatus may return or switch to the entrainment phase. For example, if the intensity of the output increases above a predetermined level and/or the subject is in the awake state for longer than a predetermined amount of time on a particular night or on each night of a series of consecutive nights, the subject may be returned to the entrainment phase.

If the criteria has been met for the subject to remain in the sleep training phase [1011], the method includes determining if the intensity of the output is zero [1012]. If so, the sleep training phase is complete and the process ends.

The methods described herein may be carried out by the apparatus or systems described herein. The methods described herein may be carried out as an algorithm by the apparatus or systems described herein.

Yet another aspect of the present disclosure provides all that is disclosed and illustrated herein.

One skilled in the art will readily appreciate that the present disclosure is well adapted to carry out the objects and obtain the ends and advantages mentioned, as well as those inherent therein. The present disclosure described herein are presently representative of preferred embodiments, are exemplary, and are not intended as limitations on the scope of the present disclosure. Changes therein and other uses will occur to those skilled in the art which are encompassed within the spirit of the present disclosure as defined by the scope of the claims.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

I claim:

1. A method for promoting continuous sleep of a subject by eliminating and/or preventing sleep associations, the method comprising:
   (a) providing an apparatus comprising at least one sensor and at least one output device;
   (b) monitoring a state of the subject using the apparatus;
   (c) determining the subject is in an awake state using the at least one sensor;
   (d) based on determining the subject is in the awake state, initiating and maintaining an output that is configured to be detected by the subject using the at least one output device, wherein the output comprises audio output;
   (e) determining the subject is in a sleep state using the at least one sensor;
   (f) halting the output including the audio output based on determining that the subject is in the sleep state in a manner that the apparatus does not produce any output while the subject is in the sleep state;
   (g) repeating at least step (b) during a sleep session,
   wherein the method further comprises modifying an intensity of the output over time until the intensity reaches zero to eliminate a sleep association,
   wherein the method is carried out over an entrainment phase and a subsequent sleep training phase, and wherein the step of modifying the intensity of the output over time is carried out during the sleep training phase,
   wherein the method further comprises, while in the entrainment phase:
   determining a total amount of time the subject is in the awake state per night; and
   switching from the entrainment phase to the sleep training phase based on determining that the total amount of time the subject is in the awake state is less than a predetermined amount of time on a particular night or on each night of a series of consecutive nights,
   wherein the method further comprises, in the sleep training phase:
   determining a total amount of time the subject is in the awake state per night;
   decreasing the intensity of the output based on determining that the total amount of time the subject is in the awake state is less than a predetermined amount of time on a particular night or on each night of a series of consecutive nights; and
   eliminating the sleep association based on sleep patterns of the subject by repeating the determining and decreasing steps until the intensity of the output is zero.

2. The method of claim 1, further comprising, in the sleep training phase:
   increasing the intensity of the output based on determining that the total amount of time the subject is in the awake state is greater than the predetermined amount of time on a particular night or on each night of a series of consecutive nights; and
   repeating the determining, decreasing, and increasing steps until the intensity of the output is zero.

3. The method of claim 1, further comprising increasing the intensity of the output based on determining that the subject is in the awake state for longer than a predetermined amount of time.

4. The method of claim 1, wherein the apparatus comprises a mattress, a mattress pad configured to be received under a mattress, a mattress pad configured to be received over a mattress, a crib, a device configured to attach to a crib, or a wearable device.

5. The method of claim 1, wherein the at least one sensor comprises a microphone and/or an accelerometer.

6. The method of claim 1, wherein the at least one output device comprises an actuator and/or a speaker.

7. The method of claim 1, wherein:
   initiating and maintaining the output is carried out after a predetermined amount of time after continuously determining the subject is in the awake state; and
   halting the output is carried out after a predetermined amount of time after continuously determining the subject is in the sleep state.

8. The method of claim 1, wherein:
   the at least one sensor and the at least one output device are each in communication with a processor, determining the subject is in the awake state and determining the subject is in the sleep state are carried out using the processor based on data captured by the at least one sensor, and
initiating and maintaining the output and halting the output are carried out based on instructions generated by the processor.

9. The method of claim 8, wherein the apparatus comprises the processor.

10. The method of claim 8, wherein the apparatus comprises a communication device, and wherein a connected device in communication with the apparatus comprises the processor.

11. The method of claim 10, further comprising modifying the operation of the apparatus based on user input on the connected device.

12. The method of claim 1, further comprising:
cycling through a plurality of different outputs;
determining which particular output or combination of outputs are most effective for promoting continuous sleep for the subject; and
using the particular output or combination of outputs that are most effective for promoting continuous sleep for the subject as the output.

13. A system for promoting continuous sleep of a subject by eliminating and/or preventing sleep associations, the system comprising:
an apparatus comprising at least one sensor and at least one output device; and
a processor in communication with the at least one sensor and the at least one output device and, during an entrainment phase, configured to:
(a) monitor a state of the subject;
(b) determine the subject is in an awake state based on data received from the at least one sensor;
(c) based on determining the subject is in the awake state, direct the at least one output device to initiate and maintain an output that is configured to be detected by the subject, wherein the output comprises audio output;
(d) determine the subject is in a sleep state based on data received from the at least one sensor;
(e) direct the at least one output device to halt the output including the audio output based on determining that the subject is in the sleep state in a manner that the apparatus does not produce any output while the subject is in the sleep state; and
(f) repeat at least operation (a) during a sleep session,
wherein, during a sleep training phase that is directly subsequent to the entrainment phase, the processor is configured to modify an intensity of the output over time until the intensity reaches zero to eliminate a sleep association,
wherein the processor is configured to:
determine a total amount of time the subject is in the awake state per night; and
switch the apparatus from the entrainment phase to the sleep training phase based on determining that the total amount of time the subject is in the awake state is less than a predetermined amount of time on a particular night or on each night of a series of consecutive nights,
wherein the processor is, during the sleep training phase, configured to eliminate the sleep association based on sleep patterns of the subject by repeatedly, until the intensity of the output is zero:
determine a total amount of time the subject is in the awake state per night; and
direct the at least one output device to decrease the intensity of the output based on the total amount of time the subject is in the awake state is less than a predetermined amount of time on a particular night or on each night of a series of consecutive nights.

14. The system of claim 13, wherein the processor is, during the sleep training phase, configured to direct the at least one output device to increase the intensity of the output based on the total amount of time the subject is in the awake state is greater than the predetermined amount of time on a particular night or on each night of a series of consecutive nights.

15. The system of claim 13, wherein the apparatus comprises a communication device, and wherein the system comprises a connected device in communication with the apparatus with the connected device comprising the processor.

16. The system of claim 13, wherein the system is configured to receive user input to: establish initial settings, select preferred sounds and motions for the output, adjust the predetermined amount of time of continuously determining the subject is in the awake state before the processor directs the at least one output device to initiate and maintain the output, adjust the intensity of the output in real time, select types of sounds of the output, adjust or select a nature of motion of the output, adjust or select a length of time for the entrainment phase, adjust or select a length of time for the sleep training phase, and/or adjust or select the rate of the decreasing the intensity of the output during the sleep training phase.

17. An apparatus for promoting continuous sleep of a subject by eliminating and/or preventing sleep associations, the apparatus comprising:
at least one sensor;
at least one output device; and
a processor in communication with the at least one sensor and the at least one output device and, during an entrainment phase, configured to repeatedly:
determine the subject is in an awake state based on data received from the at least one sensor;
based on determining the subject is in the awake state, direct the at least one output device to initiate and maintain an output that is configured to be detected by the subject, wherein the output comprises audio output;
determine the subject is in a sleep state based on data received from the at least one sensor; and
direct the at least one output device to halt the output including the audio output based on determining that the subject is in the sleep state in a manner that the apparatus does not produce any output while the subject is in the sleep state,
wherein, during a sleep training phase that is directly subsequent to the entrainment phase, the processor is configured to modify an intensity of the output over time until the intensity reaches zero to eliminate a sleep association,
wherein the processor is configured to:
determine a total amount of time the subject is in the awake state per night; and
switch the apparatus from the entrainment phase to the sleep training phase based on to determining that the total amount of time the subject is in the awake state is less than a predetermined amount of time on a particular night or on each night of a series of consecutive nights, wherein the processor is, during the sleep training phase, configured to eliminate the sleep association based on sleep patterns of the subject by repeatedly, until the intensity of the output is zero:
determine a total amount of time the subject is in the awake state per night; and
direct the at least one output device to decrease the intensity of the output based on the total amount of time the subject is in the awake state is less than a predetermined amount of time on a particular night or on each night of a series of consecutive nights.

18. A method for promoting continuous sleep of a subject by eliminating and/or preventing sleep associations, the method comprising:
(a) providing an apparatus comprising at least one sensor and at least one output device;
(b) monitoring a state of the subject using the apparatus;
(c) determining the subject is in an awake state using the at least one sensor;
(d) based on determining the subject is in the awake state, initiating and maintaining an output that is configured to be detected by the subject using the at least one output device;
(e) determining the subject is in a sleep state using the at least one sensor;
(f) halting the output based on determining that the subject is in the sleep state in a manner that the apparatus does not produce any output while the subject is in the sleep state;
(g) repeating at least step (b) during a sleep session,
wherein the method further comprises modifying an intensity of the output over time until the intensity reaches zero to eliminate a sleep association,
wherein the method is carried out over an entrainment phase and a subsequent sleep training phase, and wherein the step of modifying the intensity of the output over time is carried out during the sleep training phase,
wherein the method further comprises, while in the entrainment phase:
determining a total amount of time the subject is in the awake state per night; and
switching from the entrainment phase to the sleep training phase based on determining that the total amount of time the subject is in the awake state is less than a predetermined amount of time on a particular night or on each night of a series of consecutive nights,
wherein the method further comprises, in the sleep training phase:
determining a total amount of time the subject is in the awake state per night;
decreasing the intensity of the output based on determining that the total amount of time the subject is in the awake state is less than a predetermined amount of time on a particular night or on each night of a series of consecutive nights; and
eliminating the sleep association based on sleep patterns of the subject by repeating the determining and decreasing steps until the intensity of the output is zero,
wherein at least one of: (i) the entrainment phase has a duration of greater than zero days and 30 days or less; and (ii) the sleep training phase has a duration of greater than zero days and 30 days or less.

* * * * *